United States Patent [19]

Patrichi

[11] 4,195,368
[45] Apr. 1, 1980

[54] SURGICAL REPAIR PAD FOR DISEASE-DAMAGED JOINTS AND METHOD OF IMPLANTING THE SAME

[75] Inventor: Mihai D. Patrichi, Los Angeles, Calif.

[73] Assignee: Networks Electronic Corp., Chatsworth, Calif.

[21] Appl. No.: 910,201

[22] Filed: May 30, 1978

Related U.S. Application Data

[63] Continuation-in-part of Ser. No. 868,196, Jan. 9, 1978.

[51] Int. Cl.² .............................................. A61F 1/24
[52] U.S. Cl. ...................................... 3/1.91; 3/1.911; 3/1.912; 128/92 C
[58] Field of Search ................................. 3/1.9–1.913, 3/1; 128/92 C, 92 CA

[56] References Cited

U.S. PATENT DOCUMENTS

| | | | |
|---|---|---|---|
| 3,512,184 | 5/1970 | Grove | 3/1.913 |
| 3,879,767 | 4/1975 | Stubstad | 3/1.91 |
| 3,992,725 | 11/1976 | Homsy | 3/1.9 X |
| 4,055,862 | 11/1977 | Farling | 3/1.91 |
| 4,085,466 | 4/1978 | Goodfellow et al. | 3/1.91 |
| 4,089,071 | 5/1978 | Kalnberz et al. | 3/1.9 |

FOREIGN PATENT DOCUMENTS

| | | | |
|---|---|---|---|
| 2232002 | 1/1973 | Fed. Rep. of Germany | 128/92 C |
| 1061009 | 11/1953 | France | 128/92 C |

Primary Examiner—Ronald L. Frinks
Attorney, Agent, or Firm—Lynn H. Latta

[57] ABSTRACT

A method of repairing arthritic joints in which the bone surfaces of a knee, hip, shoulder, elbow or other articulation are cleaned of the inflammation caused by the arthritis without removing any of the bone of the joint, and then inserting into the joint a thin, dished bearing member of woven, high tensile strength material impregnated with high molecular weight polyethylene or equivalent material, and cementing one face thereof to the cleaned surface of the bone of one of the joint members, the opposite face of the bearing member being extremely smooth and polished so as to slide easily against the cleaned bone surface of the other joint member.

In preparing the bearing member, a hard metal powder, finely divided, of low thermal expansion and high corrosion and acid resistance, is intimately mixed with a colloidal dispersion of the polyethylene material and applied, in several coatings, to the surface of the bearing member which will slide against the aforesaid bone surface of the other joint member, and the last coating is polished until adequately smooth.

11 Claims, 6 Drawing Figures

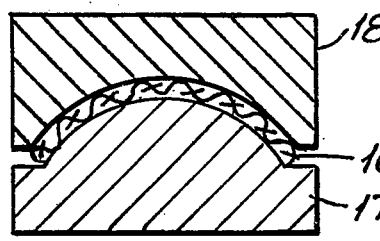
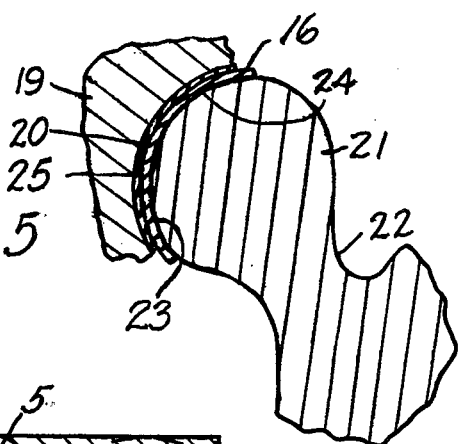
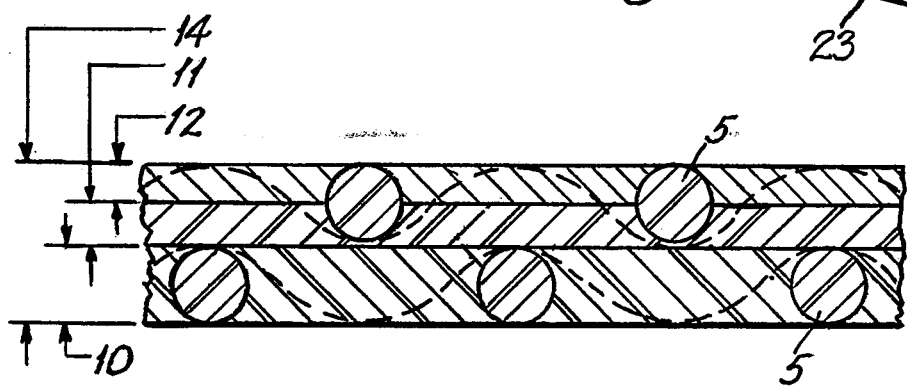
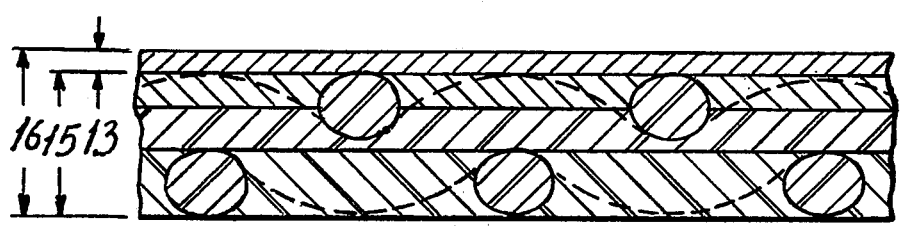
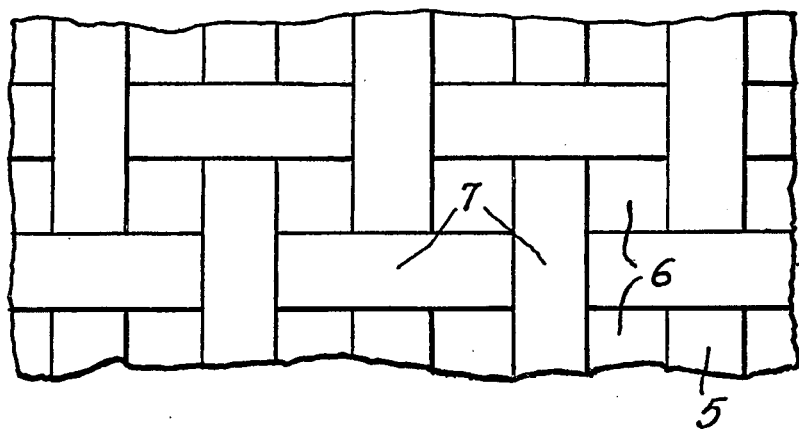
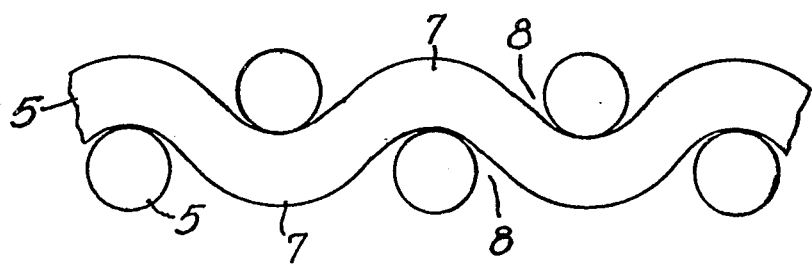

4,195,368

SURGICAL REPAIR PAD FOR DISEASE-DAMAGED JOINTS AND METHOD OF IMPLANTING THE SAME

CROSS-REFERENCES TO RELATED APPLICATIONS:

In my prior pending application Ser. No. 868,196, filed Jan. 9, 1978, I have disclosed the use of finely divided hard metal powder of low thermal expansion and high corrosion and acid resistance, intimately mixed with a colloidal dispersion of tetrafluoroethylene and a thermosetting thermoplastic adhesive and applied to one side of a backing member of woven, high tensile strength material in several applicatons so as to saturate the material to a depth of substantially the entire thickness of the woven material. The present application is a continuation-in-part of that prior application.

OBJECTS OF THE INVENTION

The present invention has as its general object to provide a prosthesis and a method of fabricating the same and of implanting it into a knee, hip, shoulder or elbow joint by cleaning the joint surfaces without removal of any of the bone material, and then attaching the prosthesis to one of the joint surfaces with the opposite side of the prosthesis (a highly polished, ultra smooth surface) in sliding contact with the other joint surface, and then closing the joint by usual surgical methods.

The principal object of the invention is to provide a prosthesis and method of implanting the same into a joint, which will provide a joint repair of long-lasting character, not subject to loosening such as is the primary cause of failure of artificial joints as presently fabricated.

IN THE DRAWING

FIG. 1 is a highly magnified cross-section of a small portion of a prosthesis embodying the invention, FIG. 1a is a similar cross-section showing the material after the drawing operation and application of the wear coat.

FIG. 2 is a plan view of the same with the top coating removed;

FIG. 3 is an edge view of a small portion of the backing material, highly magnified;

FIG. 4 is a cross-sectional view illustrating the step of molding the prosthesis; and FIG. 5 is a sectional view of a human hip joint with my prosthesis applied thereto.

DETAILED DESCRIPTION OF THE INVENTION

Referring now to the drawing in detail, I have used the reference numeral 5 to indicate the woven fabric backing member, which is of very high tensile and compressive strength, not affected materially by acids or alkalies, and capable of withstanding temperatures of up to 700° Fahrenheit. Being a woven material, it has openings, pores and cavities providing a porous surface 6. Peaks 7 are at the high points of the material, and cavities 8 are defined between them. Pores 6 extend through the fabric, and are filled with the adhesive and low-friction material which also fills the cavities 8. One particular material that may be used in the backing member is Aramid, by Du Pont. This material has the qualities desired for the backing member. However, the invention is not to be considered as being restricted to the use of this particular material. Preferably, a synthetic material is used in order to attain the combination of qualities referred to above.

The woven material is treated with several applications of adhesive/solvent, metal filler and low friction material as follows:

The adhesive is a thermoplastic, thermosetting compound adapted for solution in a suitable solvent. This material will also be referred to as a binder. Polyethylene material is advantageous because of its low friction characteristics, its durability and its extreme resistance to chemicals, but application involves difficulties which have been overcome by mixing polyethylene material of high molecular weight with the binder and metal powder in a ball mill, thus producing a good dispersion and a very smooth, uniform compound which can easily be applied by means of spraying. The polyethylene material is in powdered form, with a grain size not exceeding five microns.

The metal powder utilized by the invention is not a "soft" metal, contrary to all expectations, but a hard metal such as tungsten or a tungsten alloy, or wolfram (a tungstate of iron and manganese). Tungsten is preferred. It is utilized in the form of a very fine powder, e.g. of 0.8 micron grain size. Its concentration in the mixture of ingredients is preferably between 1% and 2% of the total. At this concentration, test results show the following:

Wear life: The antifriction mixture exhibits 0.002 inch wear at 40,000 P.S.I. (pounds per square inch) over 30,000 cycles of operation.

Peel test: The antifriction material exhibits a peel strength of 10 pounds per inch, minimum.

Titanium oxide is used as an extender in the combination, and provides a homogeneous dispersion of the metal powder in the mixture.

Referring again to the drawing, in the first step of applying the above described materials to the woven fabric member 5, a mixture of adhesive and solvent blended at a specific ratio to a homogeneous solution, is applied to the backing member 5 in a manner to saturate the same to a depth indicated at 10. The saturated material is then air or force dried at a temperature not exceeding 160° fahrenheit. Gravity is utilized in obtaining penetration of the fabric. Saturation to a depth of approximately 50% of material thickness is thus obtained.

A mixture of the adhesive/solvent solution and a tungsten metal filler such as that referred to above is then dispersed onto the backing member in a coating approximately 25% of material thickness in depth, indicated at 11 in the drawing. The material is saturated to a depth of about 75% of its thickness when the coating is absorbed into it, as indicated at 14 in the drawing. This step may be repeated in order to achieve maximum thorough saturation. Following the application of each such coating, the material is air or force dried at a temperature not exceeding 160° F.

In the next step, a mixture containing the adhesive/solvent solution, the tungsten metal filler, and the low-friction polyethylene powder referred to above, is applied to the backing member in a coating indicated at 12 in the drawing. This coating likewise has a thickness of about 25% of material thickness. The coated material, after first being air or force dried at a temperature not exceeding 160° F., is then drawn between two metallic cylinders to achieve the smoothness of the surface and the desired thickness.

Following the drawing step, there is dispersed onto the backing member, more of the adhesive/solvent tungsten, polyethylene mixture, producing a coating, indicated at 13, which protrudes not more than 0.002 inches above the peaks 7 of the backing member. Coating 13 is then air or force dried. The coated fabric is then calendered at a pressure of up to 4000 lbs. per square inch, thereby obtaining a uniform specified thickness, a highly glossy finish, and enhanced compressive strength.

The coated material is then drawn as described previously to obtain a uniform specified thickness indicated at 16 in FIG. 1. The material then has a highly glossy, smooth finish and enhanced compressive strength along with a low coefficient of friction and improved wear life, eliminating "cold flow" under "point contact" conditions.

The following table shows a specimen of some of the formulae used in a series of tests conducted during research on the invention:

| MATERIALS | 1 | 2 | 3 | 4 | 5 | 6 | 7 |
|---|---|---|---|---|---|---|---|
| Tungsten | 1 | 1 | 2.5 | 2.5 | 3 | 8 | — |
| Tio$_2$ | — | 2 | 3 | — | — | — | — |
| Polyethylene | 25 | 24 | 21.5 | 24.5 | 24 | — | 22 |
| Binder | 74 | 73. | 73 | 73 | 73 | 92 | 78 |

When tungsten powder was eliminated completely, the wear occurred rapidly, before reaching even 10,000 cycles. On a high concentration of tungsten (6–8%) the material exhibited very good resistance, but for a very short number of cycles. At a concentration between 1% and 2% of tungsten powder, the best results were obtained, as previously indicated.

Referring now to FIG. 4, the previously treated material 16 is cured under heat and pressure for a specific period of time, in a mold including male and female elements 17 and 18 respectively, resulting in a self-lubricating pad of meniscus shape suitable, for example, for surgical insertion into a human joint such as previously specified.

The lubricating material may be cut into various shapes and sizes to suit particular configurations, and then molded or bonded to fit a given joint structure. Male or female configurations may be utilized in order to present the low-friction, self-lubricating surface of the material on the convex or concave surface of the pad, as desired.

In FIG. 5 is illustrated a cross-sectional view of a human hip joint including a small portion of the ilium 19, having a hemispherical socket 20 which receives the ball 21 at the upper end of the femur 22. In repairing such a joint which has become stiffened or inflamed by arthritis, rheumatism, osteomyelitis, gout or other cause, the first step will be to obtain an impression of the male and female surfaces of the joint prior to surgery, using three-dimensional X-Ray and ultra-sonic methods to produce the shape of the bone surfaces. Having obtained the bone surface contours, there will be selected, from a family of previously prepared pads of ten or twelve different shapes, a pad of suitably conforming contour. The surgeon will then proceed to open the joint and to clean the male and female joint surfaces 20 and 21 of all inflammation and debris without removing any of the bone material. The selected pad will then be cemented to one of the joint surfaces. In cleaning the joint surfaces, the surgeon will remove all of the soft tissue, and the pad will be applied directly to the bone in order to obtain good binding between the pad, cement and bone when the pad is attached (the pad will peel off if there is intervening tissue).

FIG. 5 illustrates the pad as being attached to the femur ball 21 by a coating of cement 23, its male surface being provided with the glossy, calendered surface coating 13 of FIG. 1a, which will mate with the female joint surface 20 with a smooth sliding action in the further use of the joint by the patient. Bone, being porous, will absorb the cement and effect a welded attachment of the pad to the bone.

I claim as my invention:

1. A surgical method of repairing a disease-damaged joint of a living being, comprising the following steps:
   cleaning the ball and socket surfaces of the joint to remove extraneous material therefrom without removing any substantial amount of bone tissue;
   impregnating a porous sheet of fabric with a homogeneous solution of binder material;
   applying to one surface of the impregnated sheet a coating including binder material, said coating extending above the high points of said one surface;
   reducing said impregnated and coated sheet to a uniform specified thickness, and providing a smooth, glossy finish on said one surface;
   shaping the coated sheet between mold members having male and female shaping surfaces conforming substantially to the ball and socket surfaces respectively of the joint to be repaired, thus providing a cup-shaped pad;
   and cementing the other surface of said pad to the cleaned, mating surface of said joint, leaving said glossy surface of the pad free for smooth sliding contact with the other surface of said joint.

2. The method defined in claim 1, wherein said mating joint surface is cleaned so as to provide a bare bone surface for attachment of the pad directly thereto.

3. The method of claim 1, wherein said coating includes polyethylene material of high molecular weight, in solution.

4. The method of claim 1, wherein said solution of binder material includes a small percentage of a very finely divided metal powder, dispersed therein.

5. The method of claim 1, wherein there is dispersed in said solution of binder material, between about 1% and 2% of very fine metal powder of about 0.8 micron grain size, selected from the class including tungsten, wolfram and other tungsten alloys.

6. The method of claim 1, wherein said coating includes polyethylene material in solution, and a small proportion of a finely divided metal powder selected from the class including tungsten and tungsten alloys, plus titanium oxide functioning as an extender, providing a homogeneous dispersion of the metal powder in the coating.

7. The method of claim 1, wherein the fabric is first saturated with the coating material to a depth of about half the thickness; the saturated fabric is then dried at a temperature not exceeding 160° F.; a mixture of the coating material and a small percentage of finely divided metal selected from the class including tungsten and its alloys, is then applied to the fabric so as to increase the depth of the coating material to about 75% of fabric thickness; the fabric is then again dried; more of the coating material and metal powder mixture is then applied to the fabric so as to increase its saturation to substantially its full thickness; the saturated fabric is then dried and drawn so as to bring it to a uniform thickness.

8. The method of claim 1, wherein the fabric is first saturated with the coating material to a depth of about half its thickness; the saturated material is then dried at a temperature not exceeding 160° F.; a mixture of the coating material and a small percentage of finely divided metal powder selected from the class including tungsten and its alloys, is then applied to the fabric so as to increase the depth of the coating material to about 75% of fabric thickness; the fabric is then again dried; more of the mixture of coating material and metal powder is then applied to the fabric so as to increase its saturation to substantially its full thickness; the saturated fabric is then dried and drawn so as to bring it to uniform thickness; and, following the drawing operation, there is applied to the saturated fabric, more of the coating material and metal powder mixture so as to produce a coating which extends above the peaks of the fabric not more than about 0.002 inches; and the last mentioned coating is then dried and the coated fabric is then calendered at a pressure of up to 4000 lbs. per square inch, thereby obtaining a uniform specified thickness, a highly glossy finish, and enhanced compressive strength.

9. A repair pad of meniscus shape for surgical insertion between the ball and socket of a disease-damaged joint of a living being, comprising:
- a sheet of fabric material;
- a body of binder material saturating said fabric material, at least a portion of the thickness of said body including a finely divided hard metal powder dispersed therein;
- said saturated material being finished so as to have a highly glossy surface, a uniform specified thickness, and enhances strength.

10. A repair pad as defined in claim 9, said hard metal powder being present to the extent of about 1% to 2% of the total body of said binder material.

11. A repair pad as defined in claim 9, said hard metal powder being selected from the group including tungsten and tungsten alloys.

* * * * *